United States Patent
Larsson et al.

Patent Number: 5,196,201
Date of Patent: Mar. 23, 1993

[54] IMPLANT MATERIAL COMPOSITION, PREPARATION THEREOF AS WELL AS USES THEREOF AND IMPLANT PRODUCT OBTAINABLE THEREFROM

[75] Inventors: Kare Larsson, Bjärred; Hakan Hakansson, Lund, both of Sweden

[73] Assignee: Bioapatite AB, Malmo, Sweden

[21] Appl. No.: 600,335

[22] Filed: Oct. 19, 1990

Related U.S. Application Data

[63] Continuation-in-part of Ser. No. 424,417, Oct. 20, 1989, abandoned.

[51] Int. Cl.$^5$ .............................................. A61F 2/28
[52] U.S. Cl. ............................. 424/422; 424/423; 623/16
[58] Field of Search .................. 424/422, 423; 623/16

[56] References Cited

U.S. PATENT DOCUMENTS

| | | | |
|---|---|---|---|
| 4,192,021 | 3/1980 | Deibig et al. | 3/1.9 |
| 4,512,038 | 4/1985 | Alexander et al. | 623/16 |
| 4,516,276 | 5/1985 | Mittelmeier et al. | 623/16 |
| 4,623,553 | 11/1986 | Ries et al. | 623/16 |
| 4,629,464 | 12/1986 | Takata et al. | 623/16 |
| 4,654,464 | 5/1987 | Mittelmeier et al. | 623/16 |
| 4,828,563 | 5/1989 | Muller-Lierheim | 424/422 |
| 4,861,733 | 8/1989 | White | 623/16 |
| 4,969,906 | 11/1990 | Kronman | 623/16 |
| 5,001,169 | 3/1991 | Nathan et al. | 623/16 |
| 5,017,627 | 5/1991 | Bonfield et al. | 623/16 |

FOREIGN PATENT DOCUMENTS

| | | |
|---|---|---|
| 0126751 | of 1988 | European Pat. Off. |
| 2350826 | 12/1977 | France |
| WO88/00059 | of 1988 | PCT Int'l Appl. |

Primary Examiner—Thurman K. Page
Assistant Examiner—Amy Hulina
Attorney, Agent, or Firm—Seidel, Gonda, Lavorgna & Monaco

[57] ABSTRACT

The invention relates to an implant material composition, its preparation, and its use for restoring bone tissue in a human or animal body. The composition comprises a particulate biocompatible bone tissue substitute material distributed in a bioacceptable mixture of (a) a water-based liquid, (b) a monoglyceride, and optionally (c) a triglyceride. The ingredients (a), (b) and (c) form an L2-phase or a lamellary liquid crystalline phase, and are present in such proportions within said phases that they are capable of being transformed into a cubic liquid crystalline phase or a reversed hexagonal liquid crystalline phase when contacted with an aqueous liquid. The phase conversion imparts to the composition such a high viscosity that it functions as an implant material as defined.

35 Claims, 2 Drawing Sheets

IMPLANT MATERIAL COMPOSITION, PREPARATION THEREOF AS WELL AS USES THEREOF AND IMPLANT PRODUCT OBTAINABLE THEREFROM

This is a continuation-in-part of copending application Ser. No. 424,417 filed Oct. 20, 1989, now abandoned the entire disclosure of which is incorporated herein by reference.

Technical Field

The present invention relates to the field of implant materials for restoring bone tissues in humans or animals. More specifically the invention relates to a new, easily and consistently applicable implant material composition, to a method of preparing said composition, to uses of the same as well as to an implant product obtainable from said composition.

BACKGROUND OF THE INVENTION

The implantation of materials of different types in the human or animal body in order to replace bone portions which have been worn out or which have deteriorated due to diseases of other reasons is steadily increasing. In order to eliminate the risk of having immunological diseases different synthetic materials have come into use within this technical field. As examples of suitable materials used for said purpose there can be mentioned a metal like titanium and minerals and ceramics such as high-purity alumina, tricalcium phosphate and calcium aluminate. In the absence of risks of immunological diseases fragments from natural bone may also be considered in this respect. Especially preferred materials are, however, materials having a chemical composition and crystal structure similar to those of the materials that are built up by the living organism, such as calcium hydroxyapatite. One synthetic material of this type which has come into use for restoring bone tissue is the polycrystalline mineral calcium hydroxyapatite and particularly the non-resorbable type thereof which has the formula $Ca_{10}(PO_4)_6(OH)_2$ and which is also one of the main constituents of the bones in the body wherein the organic matrix of the bone tissue is received. Said material serves as a "climb structure" for bone tissue and prevents connective tissues from growing into the region of the bone which has been destroyed and is to be restored.

Calcium hydroxyapatite of the above-mentioned formula is manufactured by Asahi Optical Co., Ltd., Tokyo, Japan, and is marketed under the trade mark APACERAM®, which may be registered in some or all of the designated states. The material is available as performed pieces, such as tooth roots, bones for the middle ear and elements for brain surgery and also as a raw material in the form of blocks, which can be worked by sawing, milling and boring and which are of different shapes and porosities, and as a particulate material in the form of granules, i.e. particles of regular or irregular shapes, the sizes of which are of the orders from 0.1 mm to some millimeters. The blocks are used for large implants, preferably after having been properly shaped, and the granules are used for filling bone cavities as well as in combination with said blocks. Thus, since calcium hydroxyapatite is a hard and brittle material as most ceramics are, it is difficult to impart to the blocks the exact shapes needed for the actual implantations, by cutting or otherwise working the blocks, and therefore said granules are used in combination with the shape block pieces to fill out gaps or spaces existing between the shaped block pieces and the surrounding intact bone tissues.

In most cases the above-mentioned granules or particles are mixed with blood or a physiological saline solution in order to obtain a mass that is easier to apply to the desired site of the bone and to eliminate surface tension phenomena when applying said granules or particles to the bone. A major drawback to this material or technique is, however, that such a mass is not easily properly confined within the bone cavity referred to. Furthermore, when the mass has been applied to the bone, blood that may come from adjacent bleeding portions of the body or any other secreted body fluid will dilute the particulate mass and may even carry away the material from the site of application.

The primary object of the present invention is to overcome last-mentioned drawbacks and to provide an implant material which can be easily and consistently applied to the desired site of action, i.e. where the bone tissue restoration is to be made. More specifically, this means that the new implant material according to the present invention is capable of resisting dilution and any forces tending to carry away the material from the place of application.

These advantages with the present invention will be explained more in detail below as will also other objects of the invention as well as additional advantages therewith.

SUMMARY OF THE INVENTION

The primary object of the invention referred to above is achieved according to a general aspect thereof by providing an implant material composition for restoring bone tissues in a human or animal body, which composition essentially comprises or consists of a solid biocompatible bone tissue substitute material distributed in a bioacceptable mixture of (a) a water-based liquid, and (b) a monoglyceride or a vegetable or animal oil containing such a monoglyceride, and optionally (c) a triglyceride or a vegetable or animal oil containing such a triglyceride, where said ingredients (a), (b) and optionally (c) are present in the form of an L2-phase or a lamellary liquid crystalline phase, and where said ingredients are present in such proportions that said L2 or said lamellary phase is capable of being transformed into a cubic liquid crystalline phase or a reversed hexagonal liquid crystalline phase when coming into contact with or being contacted with an aqueous liquid.

According to one embodiment of the invention, an implant material for restoring bone tissue is provided comprising a particulate biocompatible non-organic bone tissue substitute and a mixture of an aqueous liquid and a monoglyceride, which material remains in the liquid phase below a predetermined temperature.

The invention also relates to a method of preparing the above-identified implant material composition. Said method essentially comprises forming the L2 or lamellary liquid crystalline phase of said ingredients (a), (b) and optionally (c), and then distributing the bone tissue substitute material therein. According to one embodiment then, a method for preparing the implant material for restoring bone tissue comprises the steps of mixing a particulate biocompatible non-organic bone tissue substitute with a mixture of an aqueous liquid and monoglyceride which remains in the liquid phase below a predetermined temperature.

Moreover, the present invention provides a method of restoring lost bone tissue in a bone of a human or animal body, which comprises applying the implant material composition as defined above to the surface of any bone or bone cavity where lost bone tissue is to be restored and allowing said composition to come into contact and/or contacting the same with an aqueous liquid in such an amount that said composition will be transformed or converted into the corresponding cubic liquid crystalline phase or the corresponding reversed hexagonal liquid crystalline phase.

According to one embodiment, the procedure for restoring lost bone tissue in a bone in a human or animal body comprises the steps of applying to the surface of the bone an implanted material of low viscosity comprising a particulate biocompatible non-organic bone tissue substitute, and a mixture of an aqueous liquid and a monoglyceride remaining in the liquid phase below a predetermined temperature, said application being below the predetermined temperature, and then bringing said implant material into contact with the aqueous liquid to change the phase of the material to a cubic liquid phase. The material thus forms a well confined plastic mass of high viscosity.

The invention also related to the composition as defined above, as to all preferable embodiments thereof, for use as an implant material composition for restoring bone tissue in a human or animal body.

Furthermore, the invention relates to the use of the above-mentioned composition for the manufacture of a product or preparation to be used as an implant material for restoring bone tissue in a human or animal body. All preferable embodiments described above in connection with the implant material composition are equally applicable to this aspect of the invention.

Finally, the invention also provides the restored implant bone tissue product per se, i.e. the product that is obtainable or obtained by contact between the implant material composition as defined above with an aqueous liquid, said product being in the state of a cubic liquid crystalline phase or a reversed hexagonal liquid crystalline line phase. All preferable embodiments disclosed above are applicable also to this aspect of the invention.

As was mentioned above, the major advantage of the present invention is that the handling of the bone substitute material will be considerable facilitated and that particles thereof are prevented from escaping from the application site. If this would happen the particles could cause irritation or complication at other places of the body.

Another advantage in connection with the invention is that the composition can be sterilized and can be stored in closed packages without any changes of properties.

Other advantages could be gathered from the present specification or should be obvious to a person skilled in the art.

DETAILED DESCRIPTION OF THE INVENTION

Figure 1:
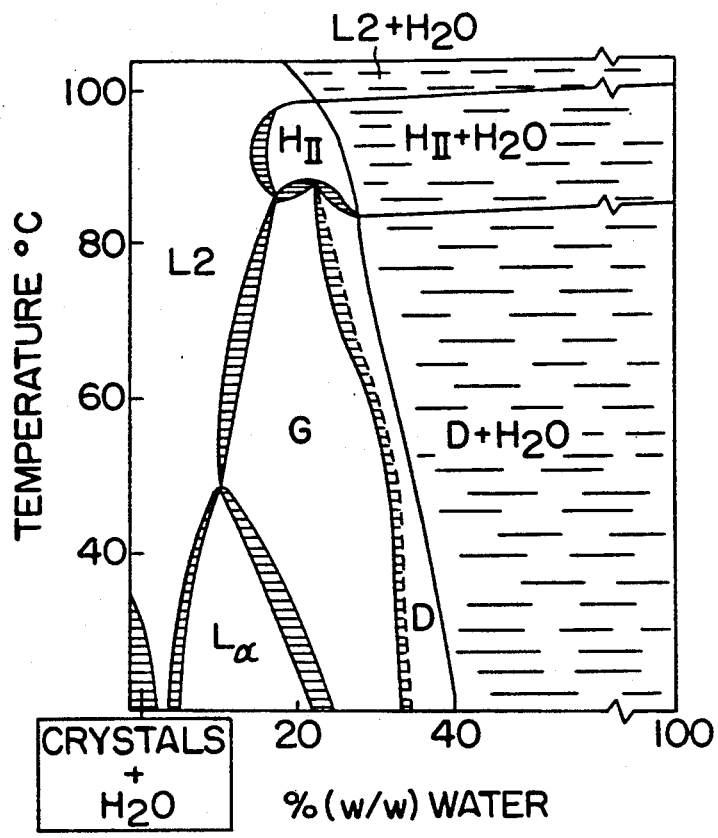
FIG. 1 is a phase diagram of a monoolein-water mixture.

The biocompatible bone tissue substitute material used according to the present invention generally is the same bone tissue substitute material that has been previously used within this technical field, as was mentioned above when describing the background of the invention. Thus, said material generally is a non-organic material in any particulate form, e.g. granular form. Moreover, it is biocompatible in the general sense of said term.

In other words the general, known principles as to the choices of biocompatible bone tissue substitute materials can be utilized when performing the present invention, but according to a preferably embodiment of the invention, said bone tissue substitute material is selected from the group consisting of a mineral, ceramic or metal.

Preferable embodiments of minerals or ceramics are calcium hydroxyapatite, alumina, tricalcium phosphate and calcium aluminate, while the dominating and preferable metal is titanium.

Especially preferably is calcium hydroxyapatite, particularly the non-resorbable type thereof which has the formula $Ca_{10}(PO_3)_6(OH)_2$. The main reason therefor is that said compound or mineral is a natural and major constituent of the bones in the body wherein the organic matrix of the bone tissue is received.

The bone tissue substitute material is distributed in a mixture of the above-mentioned ingredients (a) and (b), optionally also in the presence of (c), which mixture forms an L2-phase or a lamellary liquid crystalline phase. In this context the term "distributed" should be interpreted in a broad sense and generally means spread out in any manner throughout said L2 or lamellary liquid crystalline phase. Expressed in other ways the bone tissue substitute material can be said to be dispersed or slurried in any of the two phases referred to.

A major feature of this aspect of the invention thus is that the ingredients (a), (b) and optionally (c) (when present) are present in such amounts or proportions and conditions that they form an L2-phase or a lamellary liquid crystalline phase. In this context, it should be noted that said expressions "L2-phase" and "lamellary liquid crystalline phase", respectively, are well known to a person skilled in the art and that any more detailed descriptions thereof should not be needed. Rather, information thereabout can be found in the technical literature, and especially with reference to the nature of the L2-phase, reference is made to PCT publication WO 88/00059 and the literature mentioned therein. Thus, although said PCT publication discloses the use of an L2-phase for a completely different purpose, the principles and information found therein with reference to the L2-phase and also with reference to the lamellary liquid crystalline phase are equally applicable to said phases in connection with the present invention. For instance, said PCT publication discloses that the exact composition of the L2-phase or the lamellary liquid crystalline phase can be found in the prior art, e.g. from a ternary phase diagram. An example of such a phase diagram is also shown in the publication.

From such a diagram it can also be gathered that the L2-phase is a liquid single-phase with water-aggregates in a hydrocarbon-continuous medium.

From the above-mentioned it can also be gathered that the mixture forming said L2-phase or lamellary liquid crystalline phase can be a binary system of (a) and (b) only, or alternatively, a ternary system where ingredient (c) is also present. In both cases, however, the exact compositions to have the desired phases can easily be determined by a person skilled in the art, e.g. by means of a ternary diagram of the type referred to.

However, for the purposes of the present invention it is not sufficient to provide such proportions between the ingredients (a), (b) and optionally (c) that said L2-or lamellary phase is obtained. According to another important feature of the invention, the proportions between the ingredients present also have to be selected properly such that the composition obtained is within such specific regions or domains of the L2-phase or lamellary liquid crystalline phase that when the composition is in contact with or is contacted with an aqueous liquid it has to be capable of being transformed into the cubic liquid crystalline phase or the reversed hexagonal liquid crystalline phase. Also these two phases are well known to a person skilled in the art and therefor further information in this respect can be obtained from the prior art. PCT publication No. WO88/00059 referred to above gives some information also in this context, but especially with reference to the cubic liquid crystalline phase reference is made to European Patent specification No. 126,751. This European Patent specification discloses the use of the cubic liquid crystalline phase for completely different purposes, but as was mentioned in connection with the PCT publication, said European Patent specification is rather detailed as to the nature of the cubic liquid crystalline phase or the reversed hexagonal liquid crystalline phase, which details are equally applicable per se to the present invention.

Thus, it can be gathered that the exact composition for which a cubic liquid crystalline phase or a reversed hexagonal liquid crystalline phase is obtained is easily determined by the skilled artisan in a manner known per se, e.g. from a ternary phase diagram. From such a phase diagram one can also easily see where the starting compositions of the L2-phase or the lamellary liquid crystalline phase have to be to obtain the corresponding cubic liquid crystalline phase or reversed hexagonal liquid crystalline phase by mere addition of water or other aqueous liquid.

The basic principle of the present invention and which is utilized for the specific purposes defined herein, which is not in any way disclosed or suggested in any prior art known by us, is that the starting L2-phase or lamellary crystalline phase has the ability to change at a constant temperature its state from a liquid condition to a gel-like structure having high viscosity, solely by swelling in the water-based liquid. By mixing the bone tissue substitute material with the mixture forming said L2 or lamellary liquid crystalline phase the bone tissue substitute material will form together with any of said two phases a toothpaste-like mass or similar mass of a relatively low viscosity, which can easily be applied to a bone cavity or to a bone with an implant body mounted therein or thereupon by smearing the mass onto the surface of said bone or the surface of said bone and said implant, respectively. The viscosity of the mass will then be temporarily increased due to the increased temperature at the application site, but when the mass will come into contact with body fluid, such as blood or the humidity from soft tissue, or any other aqueous liquid, it will harden in a very short time, generally in a few seconds, to form a moldable well-confined plastic body. This sudden change in the viscosity of the implant material composition is due to the formation of the cubic liquid crystalline phase or the reversed hexagonal liquid crystalline phase when the material referred to is brought into contact with any body fluid or any other liquid present on or supplied to the site of application of the material, said material being a precursor for the formation of the cubic liquid crystalline phase or the reversed hexagonal liquid crystalline phase. In other words the phase conversion referred to is utilized in a completely new manner and for a completely new purpose, by which the previously known disadvantages within this specific technical field can be reduced or more or less completely eliminated.

In addition to the fact that the mixture of (a), (b) and optionally (c) should of course be bioacceptable, i.e., must not cause any significant side effects in contact with living cells or organisms, it could be added that generally the viscosity considerations as to the different phases refer to temperatures at or around normal body temperatures, as the composition is intended for use in contact with the body. This generally means that the viscosity of the starting phase as well as that of the transformed phase should be selected, preferably by choice of materials, so as to be proper, i.e. liquid, below a temperature of about 40° C. for the intended purpose. More specifically this means that preferable embodiments of the three ingredients (a), (b) and (c) are as follows.

The water-based liquid (a) is any liquid wherein water is the major or dominating part. This means that pure water or an isotonic salt solution is preferably utilized, but if advisable for any reason, any aqueous body fluid or other aqueous liquid may be used.

The monoglyceride (b), which can be used in the form of one single monoglyceride or as a mixture thereof, generally is a monoglyceride of an unsaturated fatty acid. Preferably said unsaturated fatty acid is an unsaturated $C_{16}$-$C_{22}$-fatty acid. An especially preferably embodiment thereof is a $C_{18}$-fatty acid, particularly monoolein. Said monoolein, which is the glyceride of oleic acid, is preferably utilized in the form of 1-monoolein or a mixture of 1-monoolein and 2-monoolein, said mixture preferably being an equilibrium mixture thereof. However, often it is not necessary to utilize the monoglyceride per se. Instead any vegetable or animal product containing the same, such as vegetable or animal oil containing the desired monoglyceride, can be used, which may even by a preferred embodiment.

The triglyceride when used as ingredient (c) generally is a triglyceride of an unsaturated fatty acid. As in connection with the monoglyceride, said triglyceride is preferably a triglyceride of an unsaturated $C_{16}$-$C_{22}$-fatty acid, more preferably a $C_{18}$-fatty acid. The triglyceride may not have to be utilized as such, but rather it may be preferable to use any natural product containing the same, such as any vegetable or animal oil containing the desired triglyceride. A preferable example of such a natural product is soybean oil. Furthermore, mixtures of triglycerides may be utilized if desired.

Although the specific ratios between the ingredients of the mixture of (a), (b) and (c) (if present) are individually determined for each specific case, e.g. from a ternary phase diagram, preferable embodiments with reference to such compositions, mainly for viscosity reasons, are the following.

A preferable weight ratio of monoglyceride (b) to water-based liquid (a) is within the range of about 97:3–85:15, a range of about 97:3–95:5 being especially preferable in many cases.

Especially in a case where a ternary system is used, preferable weight percentages of the ingredients, based on the total weight of (a)+(b)+(c), are about 2–15 percent of the water-based liquid (a), about 80–98 percent of the monoglyceride (b), and about 0–12 percent of the triglyceride (c). A preferable range of (a) is within 2–8%, especially 3–5%, while a preferable range of (b) is 85–98% or 80–90%. If present, (c) is preferably used within the range of 2–12%. A specific, interesting weight ratio within the above-mentioned range is about 5:85:10, i.e. expressed as (a):(b):(c).

Generally, although the bone tissue substitute material may be a minor volume constituent, the volume ratio of bone tissue substitute material to the total of (a) plus (b) plus (c) (when present) is within the range of 1:1–5:1, a range of about 1:1–3:1 being especially preferable for many applications. The optimum ratio, especially in the case of calcium hydroxyapatite, is around 3:1 by volume.

If the monoglyceride or triglyceride is not in the liquid state at the temperature where said L2 or lamellary liquid crystalline phase is formed, any one thereof is generally melted before the water-based liquid is added thereto.

As concerns the conditions for forming an L2 or lamellary liquid crystalline phase, reference is made to the prior art, and with reference to the distribution of the bone tissue substitute material therein, reference is made to the specification above. Thus, any suitable method of distributing a solid material in a phase of the type referred to can be utilized.

The preferable embodiments described above in connection wit the implant material composition are equally applicable to the method according to the invention of preparing said composition.

The starting L2 or lamellary liquid crystalline phase is preferably chosen so as to have a viscosity which enables the use of a conventional one-way syringe, the low viscosity implant material being received by the syringe and being ejected therefrom to the region of the bone where the mass is to be applied.

Irrespective of the method of application, however, the applied composition changes its phase to a cubic liquid crystalline phase or a reversed hexagonal liquid phase in contact with the aqueous liquid as defined above, a well-confined plastic mass of high viscosity being formed at the site of application.

After said phase conversion, the applied material may be given the final form at the application site by a plastic working of the material. The implant material can also be fixed by being covered with surrounding soft tissue which is closed by suturing.

Although the method just referred to has been described and will be more specifically described below as a method of shaping the implant product at the ultimate site of application, it is also within the scope of the invention to make a preshaping of the product outside the body in any suitable mode by bringing the implant material composition into contact with the water-based liquid and then making the final shaping and fixing in the desired bone cavity.

The preferable embodiments described above in connection with the implant material composition are equally applicable to the method of restoring lost bone tissue just described.

The invention will now be described with reference to the accompanying drawings, which show non-limiting embodiments of the invention only.

An ideal monoglyceride for use in connection with the present invention is oleic acid, inter alia because it is not easily oxidized, which might cause formation of toxic substances. Reference is made to the diagram shown in FIG. 1, which is a phase diagram for a mixture of monoolein and water indicating the relationship between temperature and water content related to the existence of the phase wherein the monoolein-water mixture is liquid and the phase wherein the monoolein-water mixture has a gel-like structure with high viscosity. If the water phase contains salts of physiological concentrations or proteins from the blood or lymph system, the diagram will not be changed.

Thus, starting from monoolein having a water content of about 4% (weight by weight) the phase is liquid in the temperature range from about 20° to 40° C., i.e. below the body temperature (about 36° C). This phase is indicated as L2 because the water molecules thereof form a reversed micellular structure. After swelling in contact with water or any other aqueous liquid, such as blood or the humidity of soft tissue, the viscous phase D ("D" stands for diamond glitter, which is the water canal structure of the phase) will be obtained, which is the cubic liquid crystalline phase. The other phases shown in FIG. 1 are: $L_\alpha$=lamellary liquid crystalline phase; $H_{II}$=reversed hexagonal liquid crystalline phase; and G=gyroid, which is also a cubic liquid crystalline phase.

An implant material of the D phase of monoolein in soft tissue and in bone tissue has been found to be perfectly biocompatible therewith and to cause no changes of inflammatory character. Probably this is due to the fact that monoolein is present in the body and will be exchanged with esterases (lipases) in the normal lipid metabolism. Another favorable factor probably is that the cubic structure is identical with the lipid structure of biological membranes, i.e. a bimolecular layer with the polar group facing outwardly towards the water medium.

In order to obtain the favorable liquid L2 phase at about room temperature, the water content of the monoolein-water mixture should preferably be within the range of from about 3.5 to 4% (weight by weight). Thus, such a liquid L2 phase has been found to be especially preferable as it imparts ideal consistence conditions to the implant material. However, higher water contents are also possible for this specific case, as then the lamellar liquid crystalline phase will be formed, which phase is also of such a viscosity that it is useful in accordance with the present invention.

Figure 2:
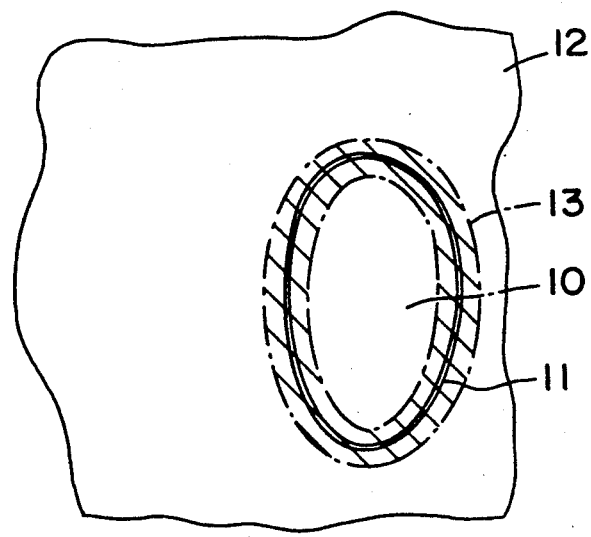
FIG. 2 is a diagrammatic plan view of a skull portion with an implant product therein.

In FIG. 2 there is shown a plate 10 obtained from a block of calcium hydroxyapatite, which plate is located and suitably fixed in an opening 11 of a scull portion 12. The implant material composition can be applied to the plate and the surrounding region of the scull indicated by hatching at 13 by dispensing the low viscosity implant material composition from a syringe wherein it has been stored, and the composition is then smeared out at least in the region 13.

When the composition is contacted with the scull, the viscosity thereof may decrease due to a temperature rise but when the composition comes into contact with any body fluid, such as blood, the viscosity thereof will increase in a few seconds so as to form a well confined mass of high viscosity which can still be plastically worked at the site of application so as to impart to the material the desired shape and to provide a smooth and tight transition between the plate and the surrounding bone of the scull. Thus, by means of the implant material, applied inaccuracies are equalized between the plate 10 and the edges of the opening 11 due to difficulties to accurately work the hard and brittle calcium hydroxyapatite blocks to the exact form of the opening.

The applied implant material may be fixed in the intended position by covering the scull and the implant region by means of surrounding soft tissue which is then closed by suturing.

Figure 3A:
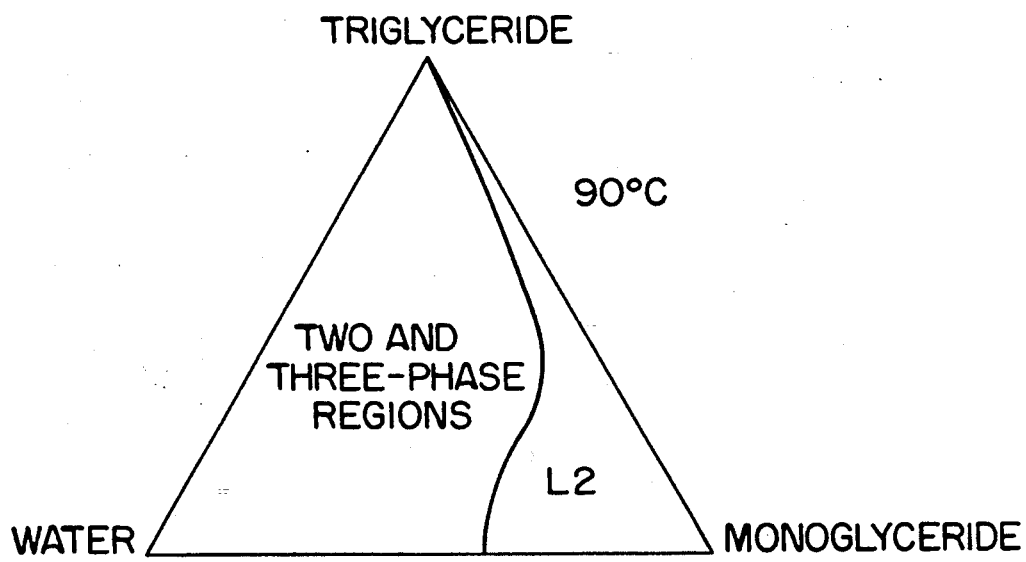
FIG. 3a and 3b show a schematic diagram for the system of sunflower oil monoglyceride/soybean oil/water at 40° C. and 90° C.
Figure 3B:
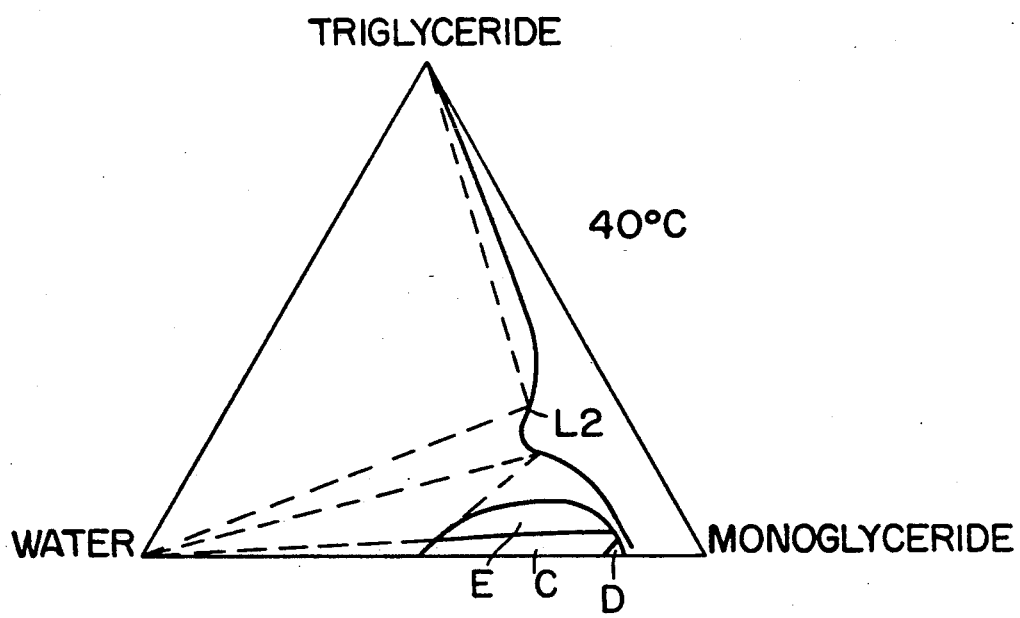

FIG. 3 shows a phase diagram for one useful composition according to the invention, i.e. sunflower oil monoglyceride/soy bean oil triglyceride/water composition at 40° C. and 90° C.

The two-phase regions and three-phase triangles are marked at 40° C. only. The meanings of the symbols are: L2, isotropic "oily" solutions; C, cubic liquid crystalline phase; D, lamellary liquid crystalline phase; and F, reversed hexagonal liquid crystalline phase. In other words, the starting implant material composition according to the invention is within the part of the L2- or D-phase where addition of water or aqueous liquid will give a composition (and a phase conversion) within any of the C- or F-phases, respectively.

The invention will also be more specifically described by means of the following non-limiting examples.

EXAMPLE 1

Monoolein is heated to a temperature just above the melting point thereof (36° C.) and not above 40° C. When the monoolein is completely melted a physiological saline solution of the same temperature (just below 40° C.) is added so as to obtain a weight ratio of monoolein:water of 96.2:3.8.

The resulting L2 phase is allowed to cool to room temperature and then granules of calcium hydroxyapatite (APACERAM®) are added, with stirring, said addition being made to a volume ratio of calcium hydroxyapatite:L2 solution of 3:1.

The implant material composition thus obtained as a toothpaste-like consistency and can be stored in closed packages, e.g. a one-way syringe, at a temperature ranging from about 0° C. to 40° C. without any changes of properties. When the composition is to be used, a temperature within the range of from 20° C. to 35° C. should be imparted thereto. In this context it should be noted that a rise of temperature will mean a lowering of the viscosity.

When applied to a bone cavity the composition sucks up body fluid and/or blood into the structure and a dramatic increase of viscosity is obtained due to the conversion of the L2 phase into a cubic liquid crystalline phase which ultimately gets saturated. The mixture is stiff but still moldable.

EXAMPLE 2

As in Example 1, monoolein is heated just over the melting point thereof (36° C.). Soybean oil is added to the melted monoolein and then a physiological saline solution is added thereto, the weight ratio of monoolein/soybean oil/water being 85:10:5.

After cooling of the resulting L2 phase to room temperature, granules of calcium hydroxyapatite (APACERAM®) are added thereto as in Example 1 to a ratio of calcium hydroxyapatite/L2-solution of 3:1 by volume. The composition thus obtained has a lower viscosity than the composition obtained according to Example 1, and the viscosity thereof will be further reduced by adding more soybean oil.

The composition behaves in a manner similar to that of the composition described in Example 1 when applied to bone in a human or animal body, that is, a phase conversion to the cubic phase is obtained.

EXAMPLE 3

As in the previous examples, monoolein is heated just above the melting point thereof (36° C.). A physiological saline solution is added thereto, the weight ratio of monoolein:water being 86:14.

After cooling the L2 phase thus obtained to room temperature, granules of the same calcium hydroxyapatite as in Examples 1 and 2 are added to a volume ratio of calcium hydroxyapatite:L2 phase of 2:1. The composition obtained has a lower viscosity than the one prepared in Example 1, but higher than that prepared in Example 2.

When applied to a bone cavity the composition sucks up body fluid and/or blood and the ultimate water content thereof increases to about 39% of the total weight when the cubic phase is saturated. During the phase conversion the viscosity increases dramatically to a stiff but still formable mixture. The time for said phase conversion depends on the body volume of the mixture, but generally it is of the order of 10–60 seconds for a volume of 1 cm$^3$.

The present invention may be embodied in other specific forms without departing from the spirit or essential attributes thereof and, accordingly, reference should be made to the appended claims, rather than to the foregoing specification, as indicating the scope of the invention.

We claim:

1. An implant material composition for restoring bone tissue in a human or animal body comprising a solid biocompatible bone tissue substitute material, said bone tissue substitute material comprising a material selected from the group consisting of minerals, ceramics and metals, and said bone tissue substitute material being distributed in a bioacceptable mixture of
   (a) a water-based liquid and
   (b) a monoglyceride,
said mixture forming an L2-phase or a lamellary liquid phase, and said (a) and (b) being present in such proportions that said L2 or lamellary phase is capable of being transformed into a cubic liquid crystalline phase or a reversed hexagonal crystalline phase when contacted with an aqueous liquid.

2. A composition according to claim 1 wherein the monoglyceride is a monoglyceride of an unsaturated fatty acid.

3. A composition according to claim 1 wherein the mixture further comprises
   (c) a triglyceride,
said mixture of (a), (b) and (c) forming an L2-phase or a lamellary liquid crystalline phase, and said (a), (b) and (c) being present in such proportions that said L2 or lamellary phase is capable of being transformed into cubic liquid crystalline phase or a reversed hexagonal liquid crystalline phase when contacted with an aqueous liquid.

4. A composition according to claim 3 wherein the triglyceride (c) is a triglyceride of an unsaturated fatty acid.

5. A composition according to claim 2 or 4 wherein the unsaturated fatty acid is an unsaturated $C_{16}$-$C_{22}$-fatty acid.

6. A composition according to claim 5 wherein the fatty acid is a $C_{18}$-fatty acid.

7. A composition according to claim 2 wherein the monoglyceride is monoolein.

8. A composition according to claim 7 wherein the monoolein comprises a mixture of 1-monoolein and 2-monoolein.

9. A composition according to claim 4 wherein the triglyceride is soy bean oil.

10. A composition according to claim 1 wherein the weight ratio of the monoglyceride (b) to water-based liquid (a) is within the range of about 97:3-85:15.

11. A composition according to claim 1 comprising about 2-15 wt. % water-based liquid (a), based on the total weight of the combination of
    (a) the water-based liquid,
    (b) the monoglyceride, and
    (c) the optional triglyceride.

12. A composition according to claim 11 comprising about 3-5 wt. % water-based liquid (a), based on the total weight of said combination.

13. A composition according to claim 11 comprising about 80-98 wt. % of the monoglyceride (b), based on the total weight of said combination.

14. A composition according to claim 13 comprising about 85-98 wt. % of the monoglyceride (b), based on the total weight of said combination.

15. A composition according to claim 11 comprising up to about 12 wet. % of the triglyceride (c), based on the total weight of said combination.

16. A composition according to claim 15 comprising about 2-12 % by weight of the triglyceride (c), based on the total weight of said combination.

17. A composition according to claim 1 wherein the metal is titanium.

18. A composition according to claim 1 wherein said bone tissue substitute material is selected from the group consisting of calcium hydroxyapatite, alumina, tricalcium phosphate, titanium and calcium aluminate.

19. A composition according to claim 18 wherein said bone tissue substitute material comprises calcium hydroxyapatite.

20. A composition according to claim 1 wherein the volume ratio of bone tissue substitute material to the combination of water-based liquid (a) and the monoglyceride (b) is within the range of 1:1-5:1.

21. A composition according to claim 3 wherein the volume ratio of bone tissue substitute material to the combination of water-based liquid (a), the monoglyceride (b) and the triglyceride (c), is within the range of 1:1-5:1.

22. A method of preparing an implant material composition as defined in claim 1 comprising forming said L2 or lamellary liquid crystalline phase from the combination of water-based liquid (a) and the monoglyceride (b), and distributing said bone tissue substitute material therein.

23. A method of preparing an implant material composition as defined in claim 3 comprising forming said L2 or lamellary liquid crystalline phase from the combination of water-based liquid (a), the monoglyceride (b) and the triglyceride (c), and distributing said bone tissue substitute material therein.

24. A method according to claim 22 comprising the further step of melting the monoglyceride (b) before adding the water-based liquid (a) thereto to form said L2 or lamellary liquid crystalline phase.

25. A method according to claim 23 comprising the further step of melting the monoglyceride (b) and the triglyceride (c) before adding the water-based liquid (a) thereto to form said L2 or lamellary liquid crystalline phase.

26. A restored implant bone tissue product obtainable by contact between the implant material composition as defined in claim 1 or 3 and an aqueous liquid, said product being in the state of a cubic liquid crystalline phase or a reversed hexagonal liquid crystalline phase.

27. Implant material for restoring bone tissue comprising:
    (a) a particulate biocompatible non-organic bone tissue substitute, said bone tissue substitute comprises a material selected from the group consisting of minerals, ceramics and metals, and
    (b) a mixture of an aqueous liquid and a monoglyceride which remains in the liquid phase below a predetermined temperature.

28. Method for preparing an implant material for restoring bone tissue comprising mixing a particulate biocompatible non-organic bone tissue substitute with a mixture of an aqueous liquid and a monoglyceride which remains in the liquid phase below a predetermined temperature, said bone tissue substitute comprising a material selected from the group consisting of minerals, ceramics and metals.

29. A composition according to claim 7 wherein the monoolein is 1-monoolein.

30. A composition according to claim 3 wherein the monoolein is 1-monoolein.

31. A composition as recited in claim 1, wherein the monoglyceride is a vegetable or animal oil containing a monoglyceride.

32. A composition as recited in claim 3, wherein the triglyceride is a vegetable or animal oil containing a triglyceride.

33. A composition as recited in claim 11, wherein the monoglyceride is a vegetable or animal oil containing a monoglyceride.

34. A composition as recited in claim 11, wherein the triglyceride is a vegetable or animal oil containing a triglyceride.

35. A composition as recited in claim 34, wherein the monoglyceride is a vegetable or animal oil containing a monoglyceride.

* * * * *